(12) United States Patent
Mohammadi

(10) Patent No.: US 11,771,382 B2
(45) Date of Patent: Oct. 3, 2023

(54) COMPUTER TOMOGRAPH

(71) Applicant: ESSPEN GMBH, Erlangen (DE)

(72) Inventor: Zahra Mohammadi, Erlangen (DE)

(73) Assignee: ESSPEN GMBH, Erlangen (DE)

( * ) Notice: Subject to any disclaimer, the term of this patent is extended or adjusted under 35 U.S.C. 154(b) by 0 days.

(21) Appl. No.: 17/761,574

(22) PCT Filed: Sep. 19, 2020

(86) PCT No.: PCT/EP2020/076204
§ 371 (c)(1),
(2) Date: Mar. 17, 2022

(87) PCT Pub. No.: WO2021/053203
PCT Pub. Date: Mar. 25, 2021

(65) Prior Publication Data
US 2022/0338821 A1    Oct. 27, 2022

(30) Foreign Application Priority Data
Sep. 20, 2019   (DE) .................... 10 2019 125 350.0

(51) Int. Cl.
*A61B 6/03* (2006.01)
*A61B 6/00* (2006.01)
(Continued)

(52) U.S. Cl.
CPC .............. *A61B 6/035* (2013.01); *A61B 6/032* (2013.01); *A61B 6/4014* (2013.01);
(Continued)

(58) Field of Classification Search
CPC ....... A61B 6/035; A61B 6/032; A61B 6/4014; A61B 6/4275
See application file for complete search history.

(56) References Cited

U.S. PATENT DOCUMENTS

| | | | |
|---|---|---|---|
| 2011/0280380 A1* | 11/2011 | Maschke ............... | A61B 6/4411 378/197 |
| 2013/0294571 A1* | 11/2013 | Kondo ................... | A61B 6/032 378/5 |
| 2020/0187882 A1* | 6/2020 | Mohammadi ........ | A61B 6/4014 |

FOREIGN PATENT DOCUMENTS

| | | |
|---|---|---|
| DE | 3426934 A1 | 5/1985 |
| DE | 10237546 B4 | 11/2007 |

(Continued)

OTHER PUBLICATIONS

International Search Report for PCT/EP2020/076204 (dated Jan. 14, 2021).

*Primary Examiner* — Chih-Cheng Kao
(74) *Attorney, Agent, or Firm* — Merchant & Gould P.C.

(57) ABSTRACT

A computer tomograph operates by rigidly arranged x-ray tubes, which are components of emitter-detector elements, which form an emitter-detector ring opened by relocating one emitter-detector element. Each x-ray tube includes a cathode emitting electrons, and an anode arrangement having an anode. Each cathode has an orientation angle relative to the geometrical center axis of the computer tomograph. A tangential plane on the focal spot of the anode has a surface normal, which includes an anode angle with the center axis. X-ray radiation emitted from the focal spot is directed in a center radiation angle to an x-ray detector axially offset relative to the x-ray tubes. The quotient from the sum of the orientation angle, radiation angle and anode angle is between two ninths and two. Each cathode, interacting with an electrode arrangement of the x-ray tubes, produces a focal spot on one of selectable positions on the anode arrangement.

16 Claims, 5 Drawing Sheets

(51) Int. Cl.
  *H01J 35/30* (2006.01)
  *H01J 35/14* (2006.01)
  *H01J 35/06* (2006.01)

(52) U.S. Cl.
  CPC .......... *A61B 6/4021* (2013.01); *A61B 6/4275* (2013.01); *H01J 35/30* (2013.01); *A61B 6/4488* (2013.01); *A61B 6/542* (2013.01); *H01J 35/064* (2019.05); *H01J 35/153* (2019.05)

(56) References Cited

FOREIGN PATENT DOCUMENTS

| | | |
|---|---|---|
| DE | 102007046278 A1 | 4/2009 |
| DE | 102010020604 A1 | 11/2011 |
| DE | 102014215548 A1 | 2/2016 |
| DE | 102016013533 A1 | 5/2018 |
| DE | 102017008810 A1 | 3/2019 |
| RU | 2164081 C2 | 3/2001 |
| WO | 2018/086737 A1 | 5/2018 |
| WO | 2018/086744 A2 | 5/2018 |
| WO | 2018/141485 A1 | 8/2018 |
| WO | 2019/042587 A2 | 3/2019 |
| WO | 2019/057338 A1 | 3/2019 |
| WO | 2019/057339 A1 | 3/2019 |

* cited by examiner

COMPUTER TOMOGRAPH

This application is a National Stage Application of PCT/EP2020/076204, filed Sep. 19, 2020, which claims benefit of Ser. No. 10/2019125350.0, filed Sep. 20, 2019, in Germany, and which applications are incorporated herein by reference. To the extent appropriate, a claim of priority is made to each of the above disclosed applications.

BACKGROUND OF THE INVENTION

The invention relates to a computed tomographic scanner, whose X-ray source-detector apparatus does not rotate during operation of the computed tomographic scanner.

Such a computed tomographic scanner is known, e.g., from WO 2018/086744 A2. This computed tomographic scanner is particularly suited for computed tomographic X-ray imaging of the human head and includes a rotationally fixed gantry having a plurality of X-ray emitters and X-ray detectors fixedly arranged about the geometric center axis of the computed tomographic scanner. Thus, the X-ray emitters and the associated detectors are offset from each other in the direction of the center axis. The gantry is displaceable as a whole in the longitudinal direction of the computed tomographic scanner, i.e., in the direction of the center axis.

An X-ray apparatus, as described in RU 2 164 081 C2, has an electron source arranged centrally in the apparatus, which electron source emits electron beams directed toward an anode provided as an X-ray source, which anode surrounds the object to be examined in an annular fashion.

Another computed tomographic scanner is described in DE 102 37 546 B4. It relates to an X-ray computed tomographic scanner having a filter, wherein the filter is matched to the directional intensity distribution of a fanned X-ray beam. This is intended to counteract the heel effect, which occurs particularly with inclined X-ray tube anodes.

SUMMARY OF THE INVENTION

The invention is based on the object [typo in original] of specifying a computed tomographic scanner with a fixed gantry, which represents a further development over the prior art, and which is characterized by a particularly good space utilization coupled with advantageous X-ray properties.

This object is achieved according to the invention by a computed tomographic scanner. The computed tomographic scanner, in a basic per-se known concept, has a plurality of X-ray tubes arranged in a fixed angular position, i.e., not rotatable, about a geometric center axis of the computed tomographic scanner. The X-ray tubes are components of emitter detector elements, which together form an emitter detector ring, which can be opened by displacing at least one of the emitter detector elements.

Each X-ray tube comprises at least one cathode intended for the emission of electrons, typically a plurality of cathodes, and an associated anode, each cathode having an alignment angle $\alpha$ defined by the mean emission direction of the electrons, to be measured with respect to the geometric center axis of the emitter detector ring. The electrons emitted from the cathode strike the surface of the anode in a basically known manner, forming a focal spot. A tangential plane centered on the focal spot has a surface normal that includes an anode angle $\beta$ with the center axis of the emitter detector ring and therefore of the whole computed tomographic scanner. The X-rays emanating by the focal spot are directed toward an X-ray detector at an average beam angle $\gamma$ to be measured with respect to a radial line passing through the focal spot and intersecting the center axis orthogonally, wherein the beam angle $\gamma$ is measured between the center beam of the X-ray beam emitted by the focal spot and said radial line. The X-ray detector is offset from the X-ray tube in the axial direction relative to the geometric center axis of the CT scanner.

The following relationship applies between the angles a, ß, and γ: $\frac{2}{3} < (\alpha+\gamma)/\beta \leq 2$ This relationship applies to all X-ray beams emanating from a focal spot. Here, each cathode acting as an electron emitter is designed in cooperation with an electrode assembly located in the same x-ray tube in order to produce a focal spot at one of at least three selectable positions on the anode assembly of the x-ray tube. The different positions of the focal spot, which can be set with one and the same electron emitter, are arranged next to one another, in particular in the circumferential direction of the emitter detector ring, i.e., distributed in different angular positions about the center axis of the computed tomographic scanner. In particular, the focal spot [typo in original], which can be generated with a single electron emitter is arranged equidistantly on the circumference of the emitter detector ring. The angular distances between the individual focal spots are, for example, a few degrees or, in the extreme case, only a fraction of a degree, wherein in each case individual focal spots are distinguishable from one another. Switching between different discrete focal-spot positions by means of controlling the electrode arrangement is also referred to as beam toggling. Thanks to beam toggling, the total number of possible focal-spot positions corresponds to a multiple of the number of electron emitters of the computed tomographic scanner. Beam toggling can be performed in the same way for the at least one beam-detector element, which can be displaced for the purpose of opening the beam-detector ring, as well as for the remaining beam-detector elements.

The invention is based on the following considerations:

The electrons emitted from the cathode of an X-ray tube installed in a computed tomographic scanner can in principle be emitted with a main propagation direction parallel to the center axis of the computed tomographic scanner, wherein means influencing the electron radiation can be provided, in particular in the form of focusing electrodes. As the electrons strike the anode of the X-ray tube, a focal spot is formed on the anode surface. Typically, X-ray tubes are designed, such that the electrons strike the anode surface at an angle not equal to 90°. For example, an essentially linear electron source results in an equally elongated shape of the focal spot.

The elongated shape of the focal spot can be optically shortened by using apertures to form an x-ray beam, which radiates obliquely from the surface of the anode.

However, it must be taken into account here that a section of the X-ray beam adjacent to the surface of the anode is weakened by the heel effect. This effect occurs all the more, the more the emitted X-rays are to be radiated away from a plane normal to the central axis of the computed tomographic scanner, in which the focal spot is located. However, radiation from said plane is necessary, if X-ray sources and associated detectors are not to be situated in a common plane. In order to mitigate the heel effect, the X-ray tube, as a whole, may be inclined with respect to the center plane of the computed tomographic scanner, i.e., by selecting an alignment angle $\alpha$ greater than zero. However, this increases the required installation space in the radial direction relative to the center axis of the computed tomographic scanner.

The said conflict of objectives is taken into account according to the invention, in that the quotient formed from the sum of the alignment angle $\alpha$ of the X-ray tube and the radiation angle $\gamma$, as the numerator, and from the anode angle $\beta$, as the denominator, is at least two-ninths and no more than two. In particular, embodiments can be realized, in which said quotient is at least two-fifths and no more than eight-fifths, e.g., at least 1 and no more than 1.6. In all cases, the quotient is dimensionless.

The possibility of opening the emitter detector ring, which does not necessarily have a circular basic shape, offers practical advantages both in terms of preparing a radiographic examination and activities, in particular medical interventions, which are carried out after a first and before a further X-ray examination, i.e., in the present case, computed tomographic examination. In particular, the position of a patient on a patient couch can remain unchanged, even if the generation of computed tomographic images is interrupted in order to perform interventions, during which the closed emitter detector arrangement would be in the way. In such a case, the movable part of the emitter detector ring can be removed from the working area, whereby the remaining, rigid part of the emitter detector ring remains in its original position required for computed tomographic imaging. Thus, during a renewed computed tomographic examination, no new adjustment of the position of the patient or the emitter detector ring is required, as long as no change in the volume to be examined is desired.

Regardless of its shape, the emitter detector ring is preferably composed of an odd number of emitter detector elements. The odd number of emitter detector elements may be used to ensure that no joint between two emitter detector elements is exactly diametrically opposite another such joint. If a focal spot is located in the edge region of an emitter detector element, i.e., near a joint between two segments of the emitter detector ring, then X-rays emanating from this focal spot strike two X-ray detectors arranged next to one another in the circumferential direction, and which are, e.g., photon-counting detectors. The use of line detectors is also possible. In this context, reference is made to WO 2019/057339 A1.

Regardless of the, e.g., straight curved shape of the individual emitter detector elements, the alignment angle $\alpha$ of the cathode, which is adjustable by the angular position of the whole X-ray tube, may be greater than zero, in particular greater than 5°. This means that the electron beam emanating from the cathode is directed at least slightly radially outwards, i.e., away from the center axis of the computed tomographic scanner. Preferably, the alignment angle is no more than 30°. For example, the anode angle $\beta$ is at least 10° and no more than 60°. In the case of an anode angle $\beta$ of 10° and any, preferably positive, alignment angle $\alpha$, a surface normal of a plane placed in the focal spot at the anode, i.e., a tangential plane, includes an angle of 10° with the center axis of the computed tomographic scanner. For example, the average radiation angle $\gamma$, which relates to the radiation of X-rays from the focal spot, is at least 5° and no more than 30°.

If, for example, an alignment angle $\alpha$ of 12°, an anode angle $\beta$ of 20° and a radiation angle $\gamma$ of 10° are selected, the said quotient is 1.1. Likewise, for example, designs can be realized, in which the alignment angle $\alpha=30°$, the anode angle $\beta=30°$, and the radiation angle $\gamma=18°$. In this case, the quotient $(\alpha+\gamma)/\beta$ is 1.6. A quotient less than 1, i.e., two-fifths, is given, e.g., for designs with an alignment angle of $\alpha=0°$, an anode angle of $\beta=30°$ and a radiation angle of $\gamma=12°$. The same value of $(\alpha+\gamma)/\beta$ is also obtained for designs with an alignment angle $\alpha$ of 6°, an anode angle $\beta$ of 45°, and a radiation angle $\gamma$ of 12°.

According to a first optional design of the computed tomographic scanner, the emitter detector ring formed by the emitter detector elements describes a segmented circular shape, wherein at least one emitter detector element designed as a segment is displaceable, in particular pivotable, relative to the other emitter detector elements. In case of several pivotable segments, they may, e.g., be rigidly connected to one another and pivoted, as a whole, out of the rest of the emitter detector ring.

Alternatively, it is possible to store several pivoting segments in the manner of a hinged door on the remaining emitter detector ring.

According to another optional design, the emitter detector ring formed by the emitter detector elements describes a polygonal shape, in particular a rectangular shape, wherein several rigidly interconnected emitter detector elements may be present and which can be pivoted relative to the rest of the emitter detector ring. For any design, in the case of a uniform design of all emitter detector elements, the control of these elements can be performed uniformly, regardless of whether an individual emitter detector element is an element intended for opening.

Control options, which may also be used in the present case, are described, e.g., in WO 2019/042587 A2. When preparing the cathodes designed to emit electrons, any solutions mentioned in the documents WO 2018/086737 A1 and WO 2018/141485 A1 may be used. Generally speaking, the X-ray tubes of the computed tomographic scanner may be designed to generate a sequence of X-ray pulses, which differ from one another in terms of various parameters, including the duration and X-ray dose of the individual pulses and the frequency of the X-ray radiation.

The anode is preferably a fixed anode, that is, an anode which does not rotate within the anode housing. The anode may either be a liquid-cooled anode, i.e., an anode through which a coolant flows, or an anode without a cooling channel. In the latter case, it is briefly referred to as an uncooled anode.

For example, anodes can be used as described in DE 10 2017 008 810 A1. As for the design of the cathodes, which may be used as electron emitters for the computed tomographic scanner, for example, the options in WO 2019/057338 A1, which claims priority from the cited patent application DE 10 2017 008 810 A1, may be selected.

In a preferred embodiment, the cathode is designed for field emission of electrons. In particular, the cathode comprises nanorods, e.g., carbon nanotubes. Examples of possible cathode materials are given in WO 2018/086737 A1.

According to an optional further embodiment, each emitter detector element comprises at least one electron emitter of a first type, and at least one electron emitter of a second type, wherein the different emitter types within an emitter detector element differ from one another in terms of their materials and/or geometry.

Depending on the dimensions of the emitter detector arrangement, the computed tomographic scanner may be suitable, for example, for examining the human head, for examinations of the chest, or for whole-body examinations.

The detectors of the computed tomographic scanner are constructed, e.g., as semiconductor detectors. With regard to particularly high sensitivity, photon-counting detectors are advantageous as components of the computed tomography scanner. In this context, reference is made by way of example to document DE 10 2014 215 548 A1.

BRIEF DESCRIPTION OF THE DRAWINGS

Several embodiments of the invention will be explained in more detail below with reference to the drawings. In the drawings.

DETAILED DESCRIPTION OF THE PREFERRED EMBODIMENT

Figure 1:
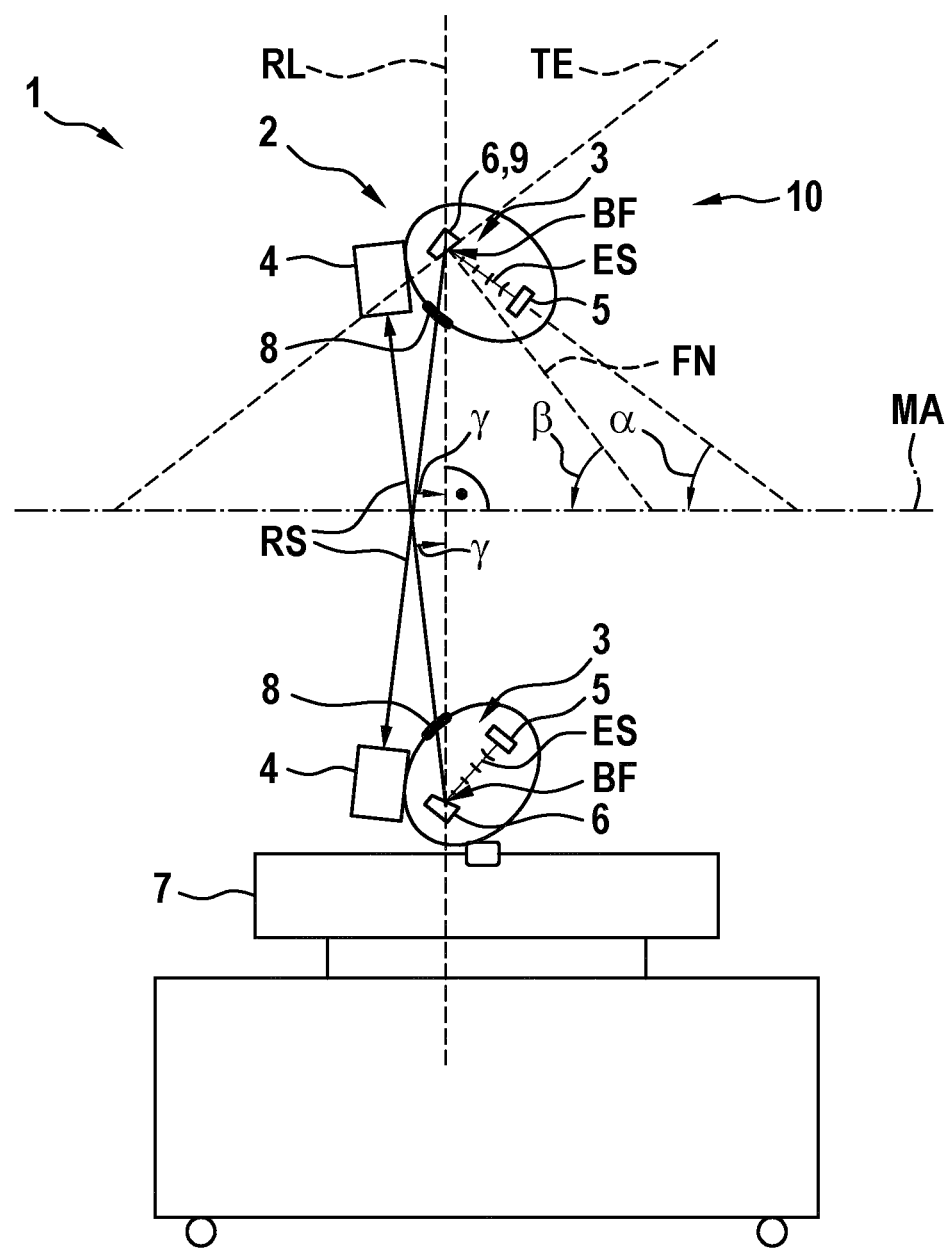
FIG. 1 shows a computed tomographic scanner in schematic representation.

Unless otherwise stated, the following explanations refer to all the exemplary embodiments.

Corresponding or in principle identically functioning parts are provided with the same reference numeral in all the drawings.

A computed tomographic scanner denoted in general by the numeral 1 is specifically designed for the examination of the human head, i.e., as a head CT. As for the basic structure of the computed tomographic scanner 1, reference is made to the document WO 2018/086744 A2 cited at the beginning.

The computed tomographic scanner 1 is shown in FIG. 1 in a roughly schematized sectional view, with the center axis of the computed tomographic scanner 1, denoted MA, located in the image plane. The z-direction of a Cartesian coordinate system is defined by the center axis MA. The x- and y-axes of the coordinate system span a plane, which is orthogonal to the image plane. A gantry of the computed tomographic scanner, denoted overall by the numeral 2, has the basic shape of a ring situated in the x-y plane. This means that the plane in which the gantry 2 lies is aligned normal to the center axis MA.

In the exemplary embodiments, the X-ray tubes 3 have an elliptical, non-circular shape in cross section, as shown in FIG. 1. Alternatively, X-ray tubes may also be used, wherein their cross-sectional shape is circular or polygonal, e.g., square, hexagonal or octagonal.

The gantry 2 comprises a plurality of X-ray tubes 3, which are distributed in a rigid angular arrangement about the center axis MA, when operating the computed tomographic scanner 1. Associated X-ray detectors 4, i.e., semiconductor detectors, are likewise arranged in an annular space about the center axis MA. The whole arrangement of X-ray tubes 3 and X-ray detectors 4 is not rotatable, and is only displaceable in the z-direction, i.e., in the longitudinal direction of the center axis MA. For this purpose, the gantry 2 is mounted on a mobile frame 7. The plane, in which the X-ray tubes 3 are located, is displaced in the axial direction, i.e., the z-direction, relative to the plane in which the X-ray detectors 4 are located.

Each X-ray tube 3 has a plurality of cathodes 5 as electron emitters. An associated anode is indicated by the numeral 6 and is assigned to an anode arrangement 9 of the corresponding X-ray tube 9. Apparatuses for influencing the electron beam indicated by ES, in particular focusing electrodes, are not shown in FIG. 1 for the sake of clarity. The electron beam ES, relative to the center of the beam, forms an angle with the center axis MA, which angle is referred to as the alignment angle α of the cathode 5. In the exemplary embodiments, the alignment angle α is greater than zero. This means that the electrons emitted from the cathode 5 have a motion component, which is radially outward relative to the center axis MA.

The electrons emitted by the cathode 5 strike a focal spot generally designated by BF on the anode 6. In the exemplary embodiments, the anode is not rotatable, i.e., is designed as a static anode. Alternatively, turntable anodes may be used. In such cases, the electron beam ES would preferably be aligned parallel to the rotational axis of the turntable anode. The alignment angle α would therefore correspond to the angle of inclination of the turntable anode rotational axis relative to the center axis MA.

A surface normal FN of a tangential plane TE, which is placed on the anode 6 and in which the focal spot BF is located, includes an anode angle β with the center axis MA. In all the exemplary embodiments illustrated in the figures, the anode angle β is at least 10° and not more than 45°. X-rays RS are emitted from the focal spot BF, although only the center beam of an X-ray beam is sketched in FIG. 1. The orientation of the X-ray radiation RS to be used for imaging is determined by apertures in a per-se known manner. The X-ray tube 3 has an X-ray window 8 for the exit of the X-rays RS.

The X-ray radiation RS emerges from the X-ray tube 3 at a mean radiation angle γ to be measured relative to a radial line RL. The radial line RL is aligned orthogonally to the center axis MA and intersects the center axis MA, as well as the center of the focal spot BF. A radiation angle γ of zero degrees would therefore mean that the X-ray radiation RS is aligned exactly in the radial direction, i.e., orthogonal to the center axis MA. Given the offset of the X-ray detectors 4 relative to the X-ray tubes 3 in the axial direction relative to the center axis MA, the radiation angle γ must be greater than zero. In the exemplary embodiments, the radiation angle γ is at least 5°, however, not more than 30°.

The sum of the radiation angle γ and the alignment angle α is at least one-twelfth of and no more than twice the anode angle β.

In the exemplary embodiments, the cathodes 5 are designed as field emission cathodes. Here, a plurality of cathodes 5 are assigned to a common anode 6 in each of the individual X-ray tubes 3. Thus, the individual X-ray tubes 3 may each have as electron emitters several cathodes 5, 25 of a uniform or different design.

Figure 6:
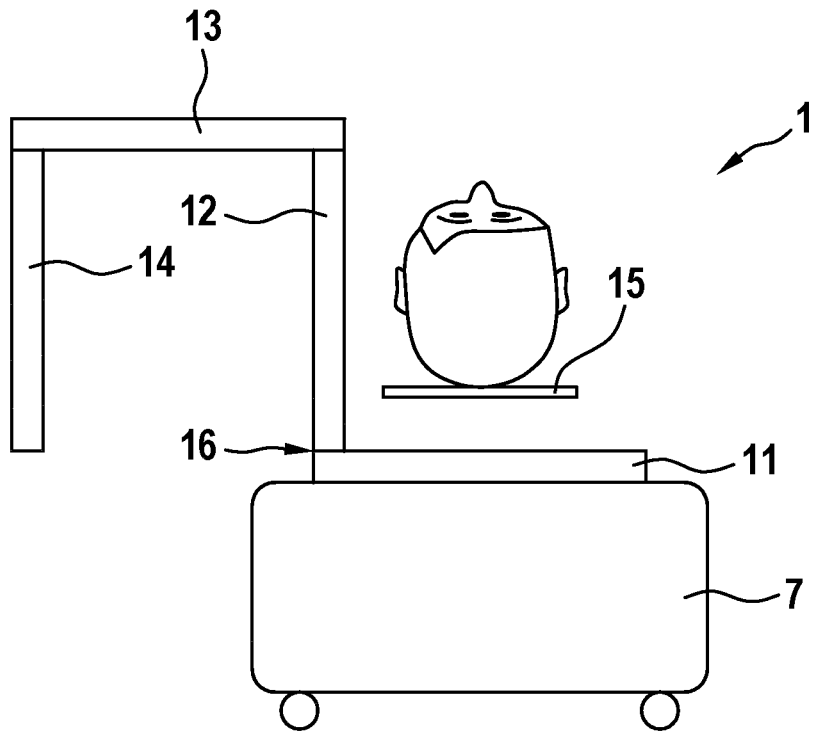
FIGS. 6 and 7 show, in views analogous to FIGS. 2 and 3, a design of a computed tomographic scanner with a rectangular emitter detector ring.
Figure 7:
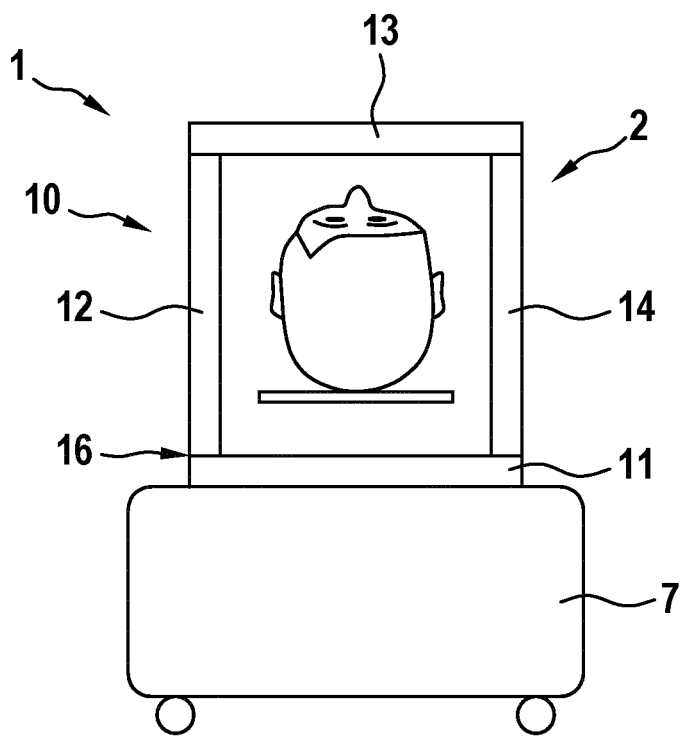

Each X-ray tube 3 is part of an emitter detector element 11,12,13,14, each of which also has an X-ray detector 4 associated therewith. The totality of the emitter detector elements 11,12,13,14 forms a non-rotating emitter detector ring 10, which represents the gantry 2 and, in the embodiments, has a circular shape according to FIGS. 1-5 and 8-9. In contrast, in the exemplary embodiment according to FIGS. 6 and 7, the emitter detector ring 10 has a square basic shape, which has no impact on its essential basic functions, both in terms of X-ray technology and its handling mode. A housing enclosing the gantry 2 is not provided. In all cases, the term "stationary," which describes the arrangement of the emitter detector ring 10, is to be understood as meaning that there is no rotation of an emitter detector unit about the center axis MA of the gantry 2, when obtaining radiographic images Rather, with the aid of X-ray tubes 3 distributed around the whole circumference of the gantry 2 and associated X-ray detectors 4, fan-shaped beams of X-ray radiation RS can be generated, each of which emanates from a focal spot BF on an anode 6 of the X-ray tube 3.

In the embodiments according to FIGS. 1-5, the emitter detector ring 10, which is composed of a total of three emitter detector elements 11,12,13, wherein the emitter detector element 11 is mounted on the frame 7 and is thus considered to be a fixed emitter detector element. [Main verb missing in the original] In contrast, the emitter detector elements 12,13 allow the emitter detector ring 10 to be opened, such that it can slide over a patient couch 15, e.g., from the side.

Figure 2:
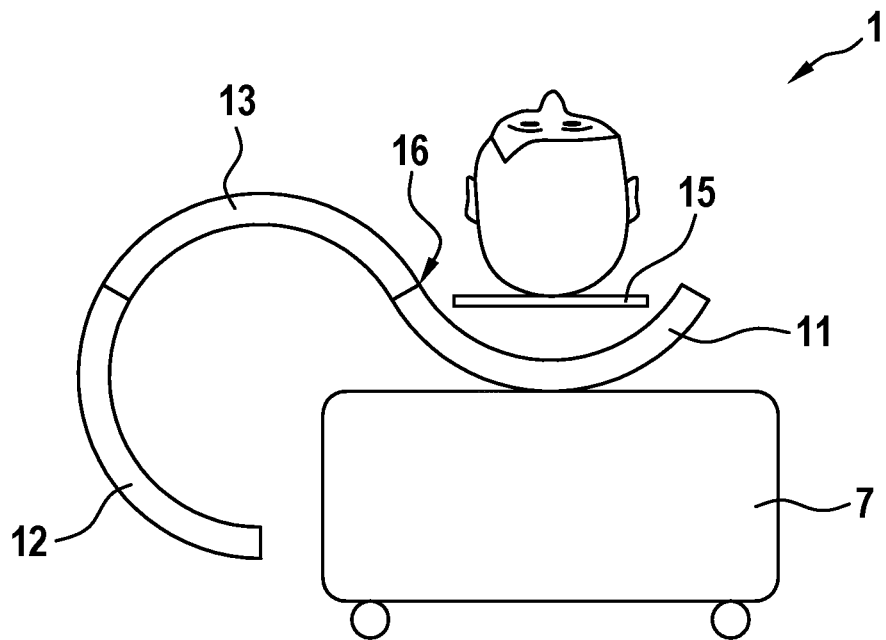
FIG. 2 shows the computed tomographic scanner according to FIG. 1 in a simplified frontal view with an opened emitter detector ring.
Figure 3:
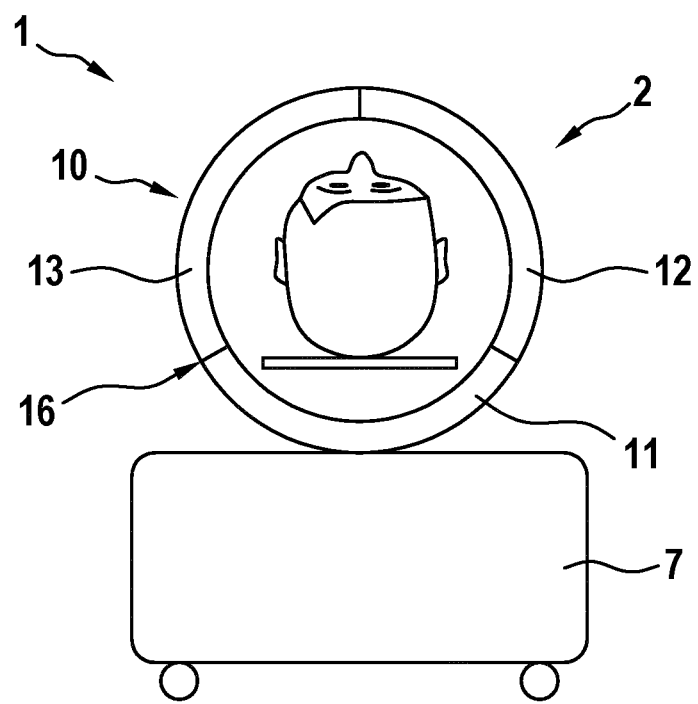
FIG. 3 shows the arrangement according to FIG. 2 with a closed emitter detector ring.

In FIGS. 1-3, in order to open the emitter detector ring 10, a single hinge 16 is provided, which is arranged between the emitter detector elements, i.e., segments 11,13. The segments 12,13, which extend over a total of approx. 240° around the circumference of the emitter detector ring 10, are, in this case, rigidly connected to one another and jointly pivoted, when the ring 10 is opened and closed.

Figure 4:
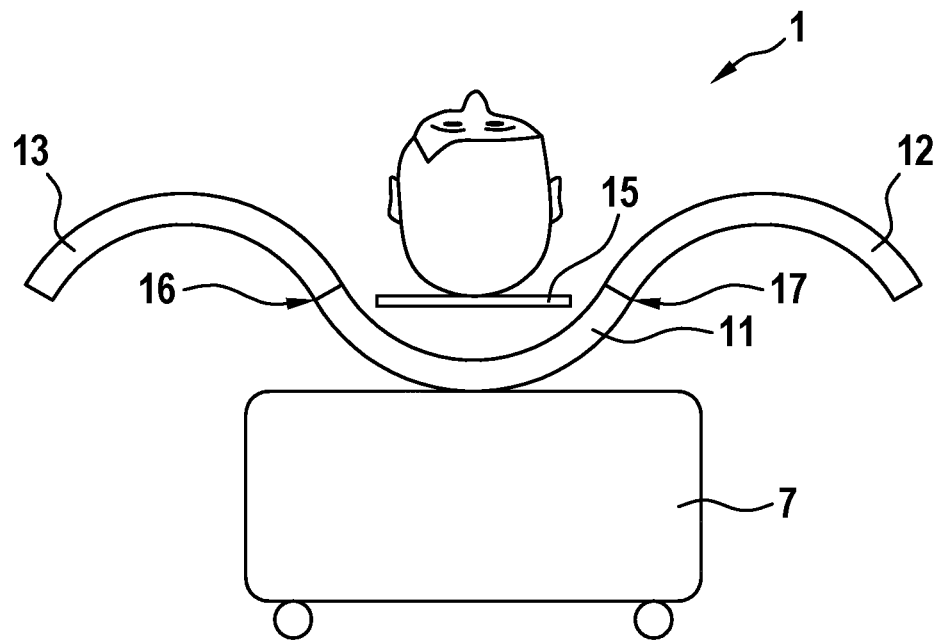
FIGS. 4 and 5 show, in views analogous to FIGS. 2 and 3, a modified design of a computed tomographic scanner.
Figure 5:
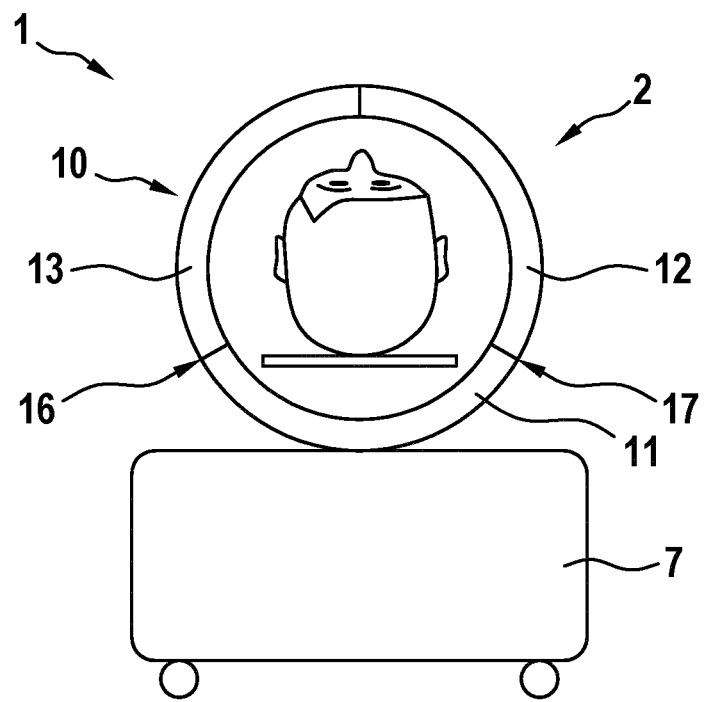

The embodiment according to FIGS. 4-5 differs from the design according to FIGS. 1-3, in that it has two hinges 16, 17, on which the segments 13 and 12, respectively, are pivotably hinged. Thus, the emitter detector elements 12,13 can be opened in the manner of a hinged door.

Figure 8:
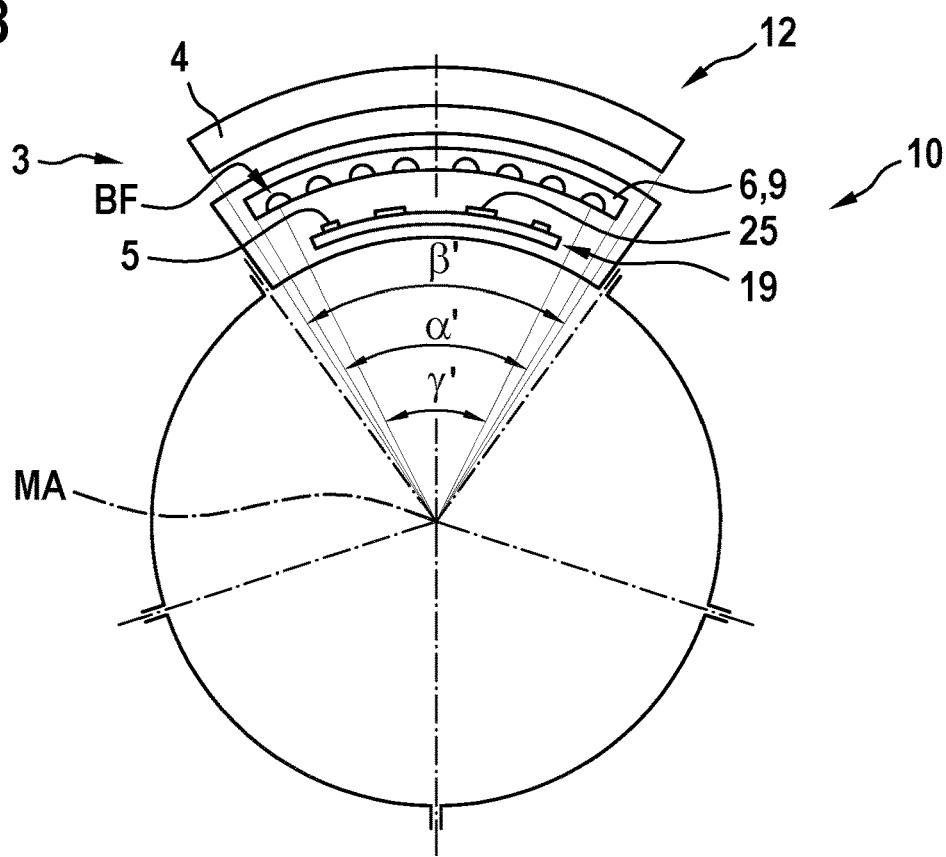
FIGS. 8 and 9 show, in schematic diagrams, details of a computed tomographic scanner with a circular segmented emitter detector ring.
Figure 9:
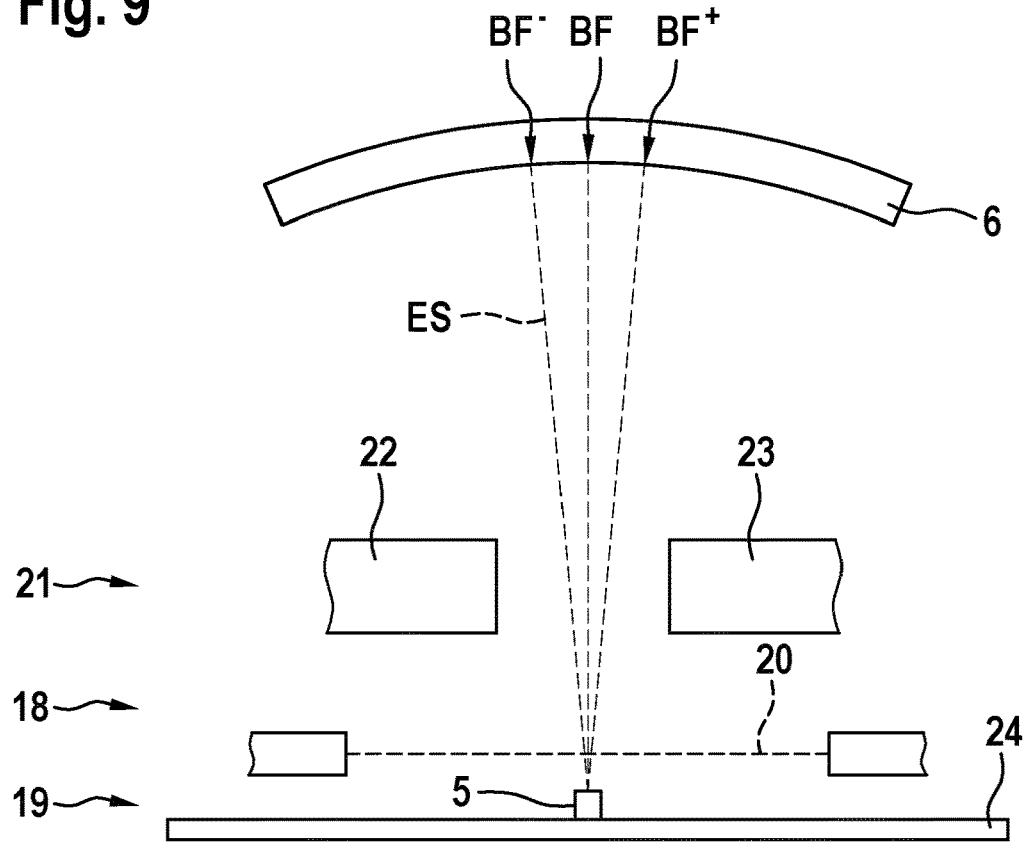

The exemplary embodiment according to FIGS. 4-5 shares similarities with the design according to FIGS. 1-3, in that several emitter detector elements 12,13,14, which together, in this case, describe a U-shape, can be jointly pivoted. The flat shape of all segments, including the fixed segment 11, makes the examination area particularly accessible, when the emitter detector ring 10 is open. FIGS. 8 and 9 illustrate details of the X-ray tubes 3 and other X-ray components, which apply to all the explained exemplary embodiments. Emitter arrangements of the X-ray tubes 3 are indicated by the numeral 18.

Each X-ray tube 3 contains an emitter assembly 19 for generating electron beams ES, which strike the anode assembly 9 in order to generate the focal spot BF. The focal spot BF need not have an approximately point-like shape. Rather, elongated focal spots BF may also be generated, e.g., in a manner known in principle, wherein the position of the focal spot BF is to be understood in each case as the position of its center point.

According to FIG. 8, the emitter assembly 19 comprises different cathodes 5, 25 in order to generate X-rays of different doses and/or wavelengths. In each case, electrons are extracted from the cathode 5, 25 by means of an extraction grid 20, wherein the electron beam ES is deflectable in a defined manner by means of an electrode arrangement 21, which comprises a plurality of electrodes 22, 23. A plurality of cathodes 5, 25 is arranged together on a circuit board 24.

The whole anode arrangement 9, which cooperates with the emitter assembly 19 of an X-ray tube 3, extends on the circumference of the emitter detector ring 10 over an angle α', which results from the number of emitter detector elements 11,12,13,14, i.e., segments of the emitter detector ring 10, wherein in the sketched arrangement in FIG. 8, five segments of equal extent, i.e., 120° segments, are provided.

The angle α', which indicates the extension of the anode arrangement 9 in the circumferential direction of the emitter detector ring 10, in FIG. 8 is slightly less than 120°. Even much closer to 72° is an angle β', which defines the extension of the X-ray detector 4 around the circumference of the emitter detector ring. In other words: Gaps formed at the periphery of the emitter detector ring 10 between the separate X-ray detectors 4 are substantially narrower than the gaps formed between the emitter arrays 18. A plurality of possible focal spot positions extends within the X-ray tube 3 over an angle γ', which is less than the angle α'.

The electrode arrangement 21 is designed to selectively direct the electron beam ES to the focal spot BF or to a focal spot $BF^+$, $BF^-$ offset relative thereto in the circumferential direction of the emitter detector ring 10. With reference to the arrangement according to FIGS. 8 and 9, focal spot $BF^+$ is deflected clockwise relative to focal spot BF, and focal spot $BF^-$ is deflected counterclockwise. The deflections of the electron beam ES, which imply an offset of the focal spot BF, are also referred to as beam toggling and make possible a particularly closely staggered placement of the focal spots $BF^-$, BF, $BF^+$ around the circumference of the emitter detector ring 10. Thus, a total number of several hundred focal-spot positions, corresponding to a multiple of the number of electron emitters 5, 25, is achievable, thus favoring a mass-saving design of the computed tomographic scanner 1, while at the same time providing high quality imaging.

REFERENCE NUMERAL LIST

1 Computed tomographic scanner
2 Gantry
3 X-ray tube
4 X-ray detector
5 Cathode, electron emitter
6 Anode
7 Frame
8 X-ray window
9 Anode arrangement
10 Emitter detector Ring
11 Emitter detector element
12 Emitter detector element
13 Emitter detector element
14 Emitter detector element
15 Patient couch
16 Hinge
17 Hinge
18 Emitter arrangement
19 Emitter assembly
20 Extraction grid
21 Electrode arrangement
22 Electrode
23 Electrode
24 Circuit board
25 Second-type cathode, electron emitter
α Alignment angle
β Anode angle
γ Beam angle
α' Angle over which the anode arrangement of a radiator-detector element extends
β' Angle over which the detector of a radiator-detector element extends
γ' Angular range in which the possible focal spots of an anode arrangement are situated
BF Focal spot (general)
BF+, BF− Focal spot generated by means of an electron emitter (in the middle position, as well as in two positions offset in the circumferential direction of the emitter detector ring).

ES Electron beam
FN Surface normal
MA Center axis
RL Radial line
RS X-ray radiation
TE Tangential plane

The invention claimed is:

1. A computed tomographic scanner comprising a plurality of X-ray tubes arranged in a fixed angular position about a geometric center axis, wherein the X-ray tubes are components of emitter detector elements which together form an emitter detector ring, which is openable by displacement of at least one of the emitter detector elements, wherein each X-ray tube comprises at least one cathode and an associated anode arrangement with at least one anode, wherein relative to a direction of emission of electrons, each cathode has an alignment angle relative to the geometrical center axis, and wherein a tangential plane applied to a focal spot of the anode has a surface normal, which includes an anode angle with the center axis, and wherein X-ray radiation emanating from the focal spot is directed at a mean radiation angle measured relative to a radial line extending through the focal spot onto an X-ray detector, which is arranged offset relative to the X-ray tube in an axial direction relative to the geometric center axis, wherein a quotient formed by a sum of the alignment angle and the radiation angle and by the anode angle is at least two-ninths and no more than two, and wherein each cathode in cooperation with an electrode arrangement of the X-ray tube is configured to generate the focal spot at one of at least three selectable positions on the anode arrangement.

2. The computed tomographic scanner according to claim 1, wherein the alignment angle is greater than zero and no more than 30°.

3. The computed tomographic scanner according to claim 1, wherein the anode angle is at least 10° and no more than 60°.

4. The computed tomographic scanner according to claim 1, wherein the mean radiation angle is at least 5° and no more than 30°.

5. The computed tomographic scanner according to claim 1, wherein the anode comprises a fixed anode.

6. The computed tomographic scanner according to claim 5, wherein the anode comprises an uncooled anode.

7. The computed tomographic scanner according to claim 5, wherein the anode comprises a liquid-cooled anode.

8. The computed tomographic scanner according to claim 1, wherein the quotient formed by the sum of the alignment angle and the radiation angle as the numerator and by the anode angle as the denominator is at least 2/5 and no more than 8/5.

9. The computed tomographic scanner according to claim 1, wherein the cathode is configured for field emission of electrons and comprises nanorods.

10. The computed tomographic scanner according to claim 9, wherein each emitter detector element has at least one emitter of a first type and one emitter of a second type, wherein the different emitter types within an emitter detector element comprise different materials and/or geometry.

11. The computed tomographic scanner according to claim 9, wherein the emitter detector elements are configured to switch between different X-ray frequencies and/or X-ray doses, wherein each focal spot is equally selectable as the source of all the adjustable X-ray frequencies and X-ray doses.

12. The computed tomographic scanner according to claim 1, wherein the emitter detector ring formed by the emitter detector elements comprises a segmented circular shape, wherein at least one emitter detector element, which is configured as a segment, is pivotable, relative to the other emitter detector elements.

13. The computed tomographic scanner according to claim 12, wherein each emitter detector element to be opened is individually pivotable.

14. The computed tomographic scanner according to claim 1, wherein the emitter detector ring formed by the emitter detector elements comprises a polygonal shape, wherein a plurality of rigidly interconnected emitter detector elements are pivotable relative to the remaining emitter detector ring.

15. The computed tomographic scanner according to claim 1, wherein all the emitter detector elements have a uniform shape.

16. The computed tomographic scanner according to claim 1, wherein the cathode is configured for field emission of electrons and comprises carbon nanotubes.

* * * * *